United States Patent
Séppala

(10) Patent No.: US 8,286,501 B2
(45) Date of Patent: Oct. 16, 2012

(54) METHOD FOR MEASURING THE FLOW PROPERTIES OF A POORLY FLOWING MATERIAL

(75) Inventor: Kari Séppala, Helsinki (FI)

(73) Assignee: Say Group Oy (FI)

( * ) Notice: Subject to any disclaimer, the term of this patent is extended or adjusted under 35 U.S.C. 154(b) by 429 days.

(21) Appl. No.: 12/671,920

(22) PCT Filed: Aug. 6, 2008

(86) PCT No.: PCT/FI2008/050451
§ 371 (c)(1),
(2), (4) Date: Feb. 3, 2010

(87) PCT Pub. No.: WO2009/019324
PCT Pub. Date: Feb. 12, 2009

(65) Prior Publication Data
US 2011/0214486 A1     Sep. 8, 2011

(30) Foreign Application Priority Data
Aug. 7, 2007   (FI) .................................... 20070592

(51) Int. Cl.
*G01F 1/00* (2006.01)
*G01N 33/00* (2006.01)

(52) U.S. Cl. ............................................. 73/861; 73/866
(58) Field of Classification Search ................... 73/861, 73/866, 861.73; 141/83; 702/48, 54
See application file for complete search history.

(56) References Cited

U.S. PATENT DOCUMENTS

| | | | |
|---|---|---|---|
| 3,178,068 A | 4/1965 | Dumbaugh | |
| 3,221,560 A | 12/1965 | Kosa | |
| 3,278,081 A | 10/1966 | Carter | |
| 3,785,529 A | 1/1974 | Dumbaugh | |
| 4,274,286 A * | 6/1981 | Gioia | 73/866 |
| 4,320,657 A | 3/1982 | Johnson, III | |
| 4,630,755 A * | 12/1986 | Campbell | 222/56 |
| 2004/0007285 A1 | 1/2004 | Finke et al. | |
| 2006/0065063 A1* | 3/2006 | Kalidindi | 73/863.57 |
| 2009/0078029 A1* | 3/2009 | Matsusaka et al. | 73/54.41 |

* cited by examiner

*Primary Examiner* — Hezron E Williams
*Assistant Examiner* — Nathaniel Kolb
(74) *Attorney, Agent, or Firm* — Skinner and Associates

(57) ABSTRACT

Method and device for measuring the flow properties of a poorly flowing material. The material is placed in a measuring reservoir (2) equipped with a flow opening (6) of the desired size (2), an upwards and downwards motion is induced in the reservoir (2) with the aid of an operating device (4), to which the reservoir (2) is attached, and the flow properties of the material are determined.

11 Claims, 1 Drawing Sheet

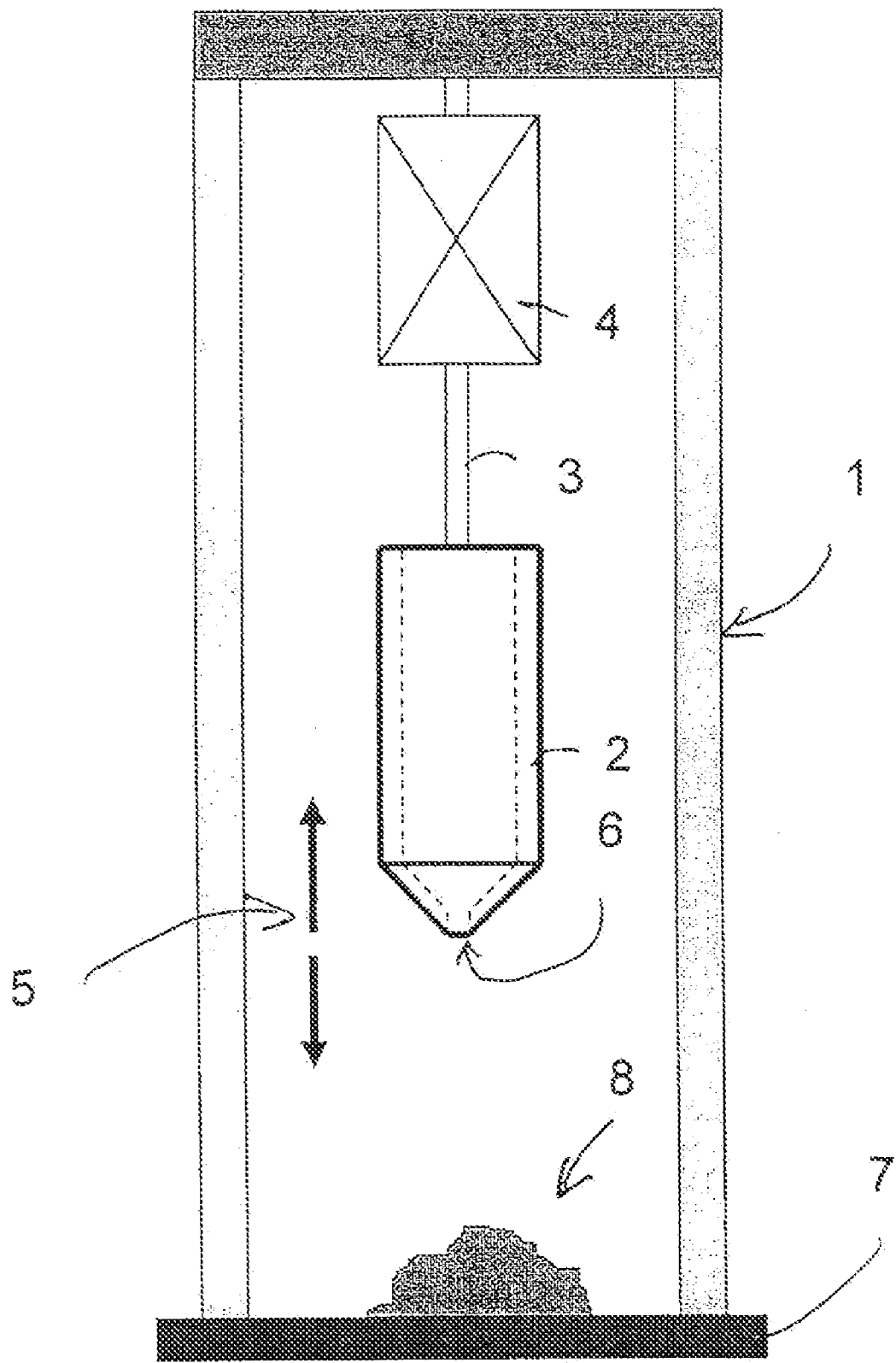

METHOD FOR MEASURING THE FLOW PROPERTIES OF A POORLY FLOWING MATERIAL

The present invention relates to a method for measuring the flow properties of a poorly flowing material, particularly a powder.

The method and the device for use in the method are also suitable for measuring the flow properties, i.e. the 'viscosity' of poorly flowing gel-like substances, various suspensions, and paste-like substances, for example, mustard or ketchup.

In many applications in the fields of chemistry and medicine, the flow properties of a specific, especially a powdery material need to be measured. In practice, it has been very difficult to develop a reliable method, so that there is a great need for a method of this kind.

As stated, the powder to be measured flows poorly. This means that in situations, in which some other material flows evenly through the measuring device, giving reliable and repeatable results, a poorly flowing material will remain firmly in the measuring device, making it impossible to obtain results.

Though attempts have been made to solve the problem, there is simply no good and cheap device for measuring a poorly flowing material.

The present device is intended to create a method, with the aid of which the flow properties of a material of the kind referred to can be reliably approximated.

The aforementioned and other benefits and advantages of the present invention are achieved in the manner described as characteristic in the accompanying claims.

In brief, the basic principle of the invention is that the material need not flow continuously, in order to determine its flow properties, but instead if it is made to flow at intervals, this will give a sufficiently accurate picture of its properties.

In the following, the invention is examined in greater detail with reference to a schematic drawing of the device according to the invention, which shows one embodiment of the invention.

The FIGURE shows the device's body 1, which can also be any shield whatever that ensures more or less undisturbed working conditions. The material to be measured is placed in a reservoir 2 made of a suitable material, the lower part of which is especially funnel-like. The reservoir can also be single-use. The reservoir can also be surfaced with a suitable coating, in order to prevent the powder from adhering. This is assumed to have a beneficial effect on the resolution and repeatability of the measurement.

In the lower surface of the reservoir, there is a flow opening 6, the size of which can be altered by changing the entire reservoir, or by using a suitable accessory with an opening of the desired size.

Obviously a funnel-like or conical bottom part for the reservoir will be quite suitable for many purposes. However, when necessary, the bottom part can be of some other shape, such as flat, convex, convex, or even asymmetrical. I.e. the flow opening can be asymmetrically at the side of the base, or there can be two or more openings. The base can also be of a mesh material, if required by the material being measured.

A suitable suspension device 4 is used to attach the reservoir 2 to an operating device 4, which is, in turn, suspended by suitable attachments from fixed structures, such as the body of the device, or the roof of the measuring chamber 1. The operating device 4 is intended to induce a motion in the reservoir 2 like that shown by the arrows 5. The motion is vertical. The amplitude and frequency of the motion, as well as its sharpness and profile are adjusted for each type of material on the basis of empirical information.

The intention is for the motion induced in the measuring reservoir by the operating device 4, first upwards and then returning downwards, particularly when using a powdery sample, to cause the sample batch being measured to jump in the reservoir, so that the return of the material to the bottom of the reservoir will cause a certain amount of the material being measured to flow in any event out of the reservoir 2 through the flow opening 6, before the flow stops due to the properties of the substance. By repeating the vertical motion at a specific amplitude and frequency, a periodic flow of the material will be achieved.

All in all, the pulse ratio of the motion induced by the operating device, the vertical velocity of the pulse, and the length and frequency of the stroke are selected so as to break the arching typical of the type of material being measured, i.e. the formation of a cover, by means of these selections, thus making the material to move.

When measuring gel-like or other liquid or paste-like substances like ketchup or mustard, which do not arch as such, it may be necessary to use, for example, a sine or triangular-shaped shaking profile.

The shaking profile can also vary periodically, or its profile can be freely programmed as required using a suitable control program. The profile can be depicted by a square wave, the upper horizontal part of which is substantially shorted than the lower horizontal part. In practice, this means that a rapid upwards motion occurs, followed by a short stop at the top after which the motion returns to its initial position, and there is then a wait for a specific time. During the latter wait, the material flows out of the measuring device, the flow then terminating either fully or substantially during this period.

According to the invention, the flow properties are evaluated on the basis of how long it takes for a specific amount of material to flow out of the reservoir. Evaluation can take place by weighing the amount of material and comparing it to the time taken. In certain cases, the measurement of volume can be used instead of, or together with the weight of the material.

The measurement can be assisted by a scales arrangement, such as the plate marked with the reference number 7, onto which the material flows, and which plate is connected to a scales system. Naturally, there can also be some kind of weighing system connected to the reservoir 2.

It may also be necessary to study the shape of the flow heap 8. For example, it is possible to measure the angle of repose of the heap created.

Many other systems, besides the aforementioned scales system can be used to detect the end of the flow of the material being measured, i.e. when all of the material has flowed out of the measuring reservoir. One system is based on using light. For example, light can be projected through the measuring reservoir, so that the end of the material will mean that the light beam can pass through the reservoir and can be detected from the base. In a more highly developed system, a photoelectric cell, for example, can be used to detect the light beam. The entire detection system can be easily automated according to a specific program.

Practical tests have shown that even poorly flowing materials can be easily measured reliably in terms of flow properties using an apparatus according to the invention.

The operating device can be any device at all, which can be used to create a preferably adjustable vertical motion. Many different kinds of application for vibration of this kind are in use in other fields. Examples that can be given include electrical applications, such as solenoid-type devices, a device based on an eccentric, and similar. Mechanical devices too can be used for this purpose.

The invention can be varied in many ways while nevertheless remaining within the scope of protection defined by the basic principle described above and the accompanying Claims.

The invention claimed is:

1. Method for measuring the flow properties of a poorly flowing material, in which method the material is placed in a measuring reservoir (2) equipped with a flow opening (6) of a desired size, an upwards and downwards motion is induced in the reservoir (2) with the aid of an operating device (4), to which the reservoir (2) is attached, characterized in that the vertical velocity and length of stroke of the motion caused are selected to be such that, when the upward motion stops, the material continues to rise, breaking the cover of the possibly arched material, and the delay time in the lower position of the motion is selected to be such that the flow of the material in the case of the cycle in question has substantially or entirely terminated, and the flow properties of the material are determined from the duration of the flow.

2. Method according to claim 1, characterized in that the amplitude and frequency of the motion induced by the operating device are adjusted according to the material being measured.

3. Method according to claim 1, characterized in that the measuring reservoir (2) is equipped with a conical bottom.

4. Method according to claim 1, characterized in that the measuring reservoir (2) is equipped with a concave, flat, convex, or asymmetrical bottom.

5. Method according to claim 1, characterized in that the pulse ratio of the motion induced by the operating device (4) is adjusted in such a way that the measuring reservoir (2) is down for most of the pulse, rather than up.

6. Method according to claim 1, characterized in that the shaking profile of the motion is continuous and/or periodic and can be altered according to the desired program to induce, for example, a sine or triangular-shaped motion profile.

7. Method according to claim 1, characterized in that an operating device (4) is used, which is electrically operated.

8. Method according to claim 1, characterized in that the device is also equipped with a scales device.

9. Method according to claim 1, characterized in that the device is equipped with a means based on light for detecting the end of the material being measured.

10. Method according to claim 9, characterized in that the device based on light is intended to send light through the measuring reservoir and, also comprises a photoelectric cell, for detecting the light travelling through the reservoir.

11. Method according to claim 1, characterized in that the measuring reservoir is coated with a coating reducing the adhesion of the substance being measured.

* * * * *